United States Patent
Gan

(10) Patent No.: US 6,840,107 B2
(45) Date of Patent: Jan. 11, 2005

(54) ACOUSTIC MICROSCOPE

(75) Inventor: Woon Siong Gan, Singapore (SG)

(73) Assignee: Acoustical Technologies Pte Ltd., Singapore (SG)

( * ) Notice: Subject to any disclaimer, the term of this patent is extended or adjusted under 35 U.S.C. 154(b) by 0 days.

(21) Appl. No.: 10/275,230

(22) PCT Filed: Apr. 25, 2001

(86) PCT No.: PCT/SG01/00070
§ 371 (c)(1),
(2), (4) Date: Nov. 4, 2002

(87) PCT Pub. No.: WO01/86281
PCT Pub. Date: Nov. 15, 2001

(65) Prior Publication Data
US 2003/0101820 A1 Jun. 5, 2003

(30) Foreign Application Priority Data
May 5, 2000 (GB) .............................. 0010972

(51) Int. Cl.[7] ................................ G01N 9/24
(52) U.S. Cl. ........................................ 73/606; 73/642
(58) Field of Search .................... 73/606, 617, 620, 73/627, 642, 644, 647

(56) References Cited

U.S. PATENT DOCUMENTS

| 4,550,609 | A | * | 11/1985 | Johnson | 73/642 |
| 4,655,083 | A | * | 4/1987 | Chubachi | 73/606 |
| 4,699,150 | A | * | 10/1987 | Kawabuchi et al. | 600/446 |
| 5,060,201 | A | * | 10/1991 | Ishikawa et al. | 367/7 |
| 5,123,067 | A | * | 6/1992 | Avelange et al. | 385/14 |
| 5,176,140 | A | * | 1/1993 | Kami et al. | 600/459 |
| 5,216,695 | A | | 6/1993 | Ross et al. | 375/59 |
| 5,384,467 | A | * | 1/1995 | Plimon et al. | 250/554 |
| 5,549,003 | A | * | 8/1996 | Drescher-Krasicka | 73/606 |
| 5,745,067 | A | | 4/1998 | Chou et al. | 341/156 |
| 5,922,961 | A | | 7/1999 | Hsu et al. | 73/606 |
| 6,382,824 | B1 | * | 5/2002 | Prasad et al. | 362/551 |
| 6,609,425 | B2 | * | 8/2003 | Ogawa | 73/608 |

FOREIGN PATENT DOCUMENTS

| GB | 2242270 A | 9/1991 |
| WO | WO 88/00710 | 1/1988 |
| WO | WO 00/69357 | 11/2000 |

* cited by examiner

Primary Examiner—Hezron Williams
Assistant Examiner—Jacques M. Saint-Surin
(74) Attorney, Agent, or Firm—Bowditch & Dewey, LLP

(57) ABSTRACT

An acoustic microscope is disclosed having an acoustic lens formed of fused metal and glass. A high speed analogue to digital converter and a pulse generator/receiver are also disclosed. Automated V(z) curve measurement produces quantitative elastic properties of the specimen. (C) and (B) scans are sliced and a simulated three-dimensional image is formed therefrom.

22 Claims, 18 Drawing Sheets

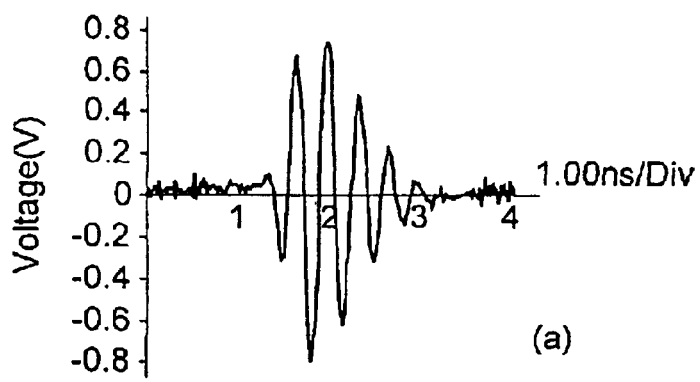
(a)
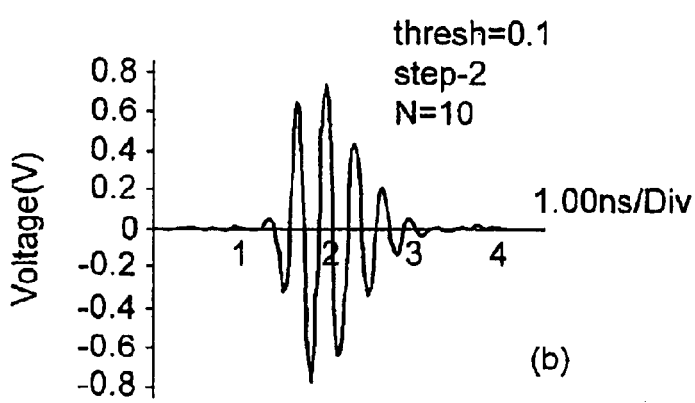
(b)
(c)
FIG. 8

BEFORE CURVE FITTING  AFTER CURVE FITTING (a)  (b)  (c)

(a) SURFACE IMAGE   (b) MID-LAYER IMAGE   (c) BOTTOM LAYER IMAGE

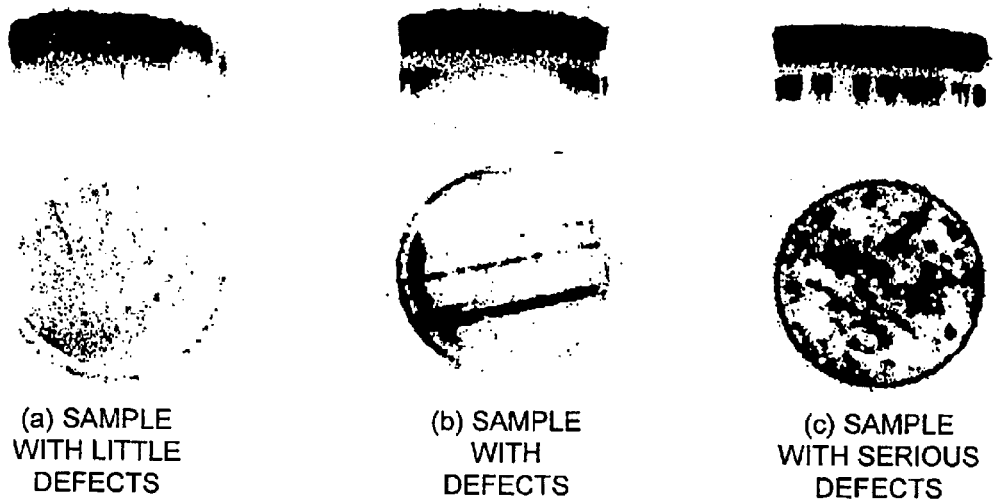
(a) SAMPLE WITH LITTLE DEFECTS
(b) SAMPLE WITH DEFECTS
(c) SAMPLE WITH SERIOUS DEFECTS
FIG. 16
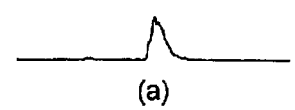
(a)
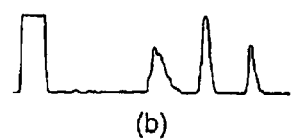
(b)
(c)
FIG. 17

FIG. 23
FIG. 24
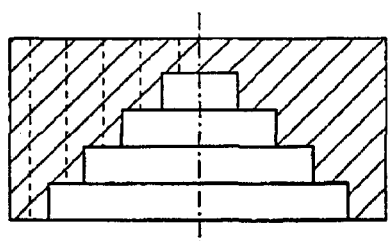 
(a) FIG. 25 (b)
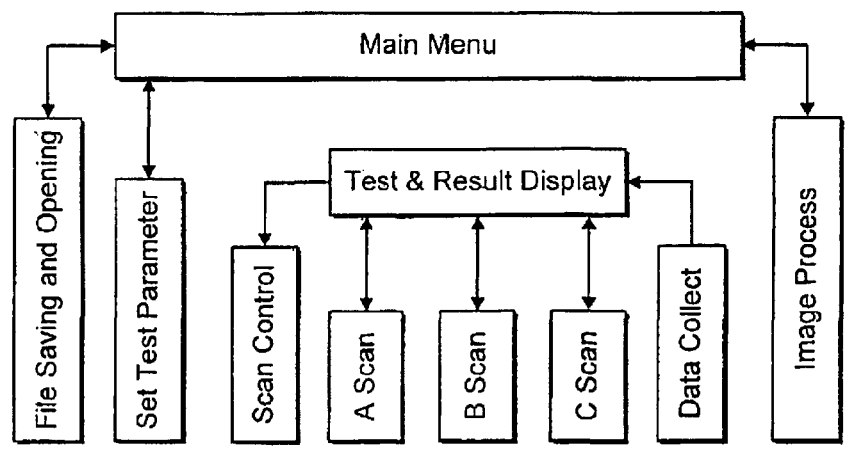
FIG. 26

ACOUSTIC MICROSCOPE

This invention relates to the fields of ultrasonic testing, imaging, analysis and processing, and more particularly relates to an acoustic microscope. Such microscopes are widely used in nondestructive testing, observation and analysis in the material, electronics, mechanics and medical fields.

GB 2311858 relates to an ultrasonic imaging system. Ultrasonic waves are, generated by laser beams. Reflected waves are detected and converted into digital signals. The digital signals are processed using a synthetic aperture focussing technique in order to obtain focussed images.

Ultrasonic testing has been known for several decades. The testing devices most widely used are industrial A scan flaw detector, medical B scan ultrasonic scanner, C scan ultrasonic imagery machine and other advanced products, such as acoustic microscopes.

A, B and C scan modes are the three basic modes of ultrasonic imaging classified under the pulse echo techniques. When an ultrasonic wave in pulse form impinges on a discontinuity it will be reflected and the reflected pulse can be recorded. This reflected pulse carries information on the discontinuity. This is quite similar to the formation of echo and hence the name pulse echo.

The A scan is the simplest form of ultrasonic imaging. It just records the reflected pulse or signal and is one dimensional and no images are formed.

The B scan or brightness mode scanning, provides a two dimensional, cross sectional reflection image of the object that is scanned. It gives the side view of the object. A B scan image is formed by sweeping a narrow acoustic beam through a plane and positioning the received echoes on a display such that there is a correspondence between the display scan line and the direction of acoustic propagation in the material. Generally the same transducer is used to both send and receive the acoustic signals. A fundamental feature of a B scan image is that one of the dimensions is inferred from arrival time of each of a short acoustic pulse as they reflect from structures along a (presumed) straight-line path. Signals received from structures close to the transducer arrive earlier than signals received from structures far from the transducer. The other (transverse) dimension is obtained by moving the transducer (either physically by mechanical means or apparently by electronic means) so that a different straight line path through the object is interrogated by another short acoustic pulse. This process is continued until the entire object region of interest is scanned. Some means of tracking the propagation path through the object is required in order to unambiguously define the image.

The C scan provides a two-dimensional orthographic image of an object. It gives the top view of the object. Unlike, the B scan, where one dimension of the image is inferred from the arrival time of an acoustic pulse, time plays no primary role in either of the two image dimensions of a C-scan. In a reflection C-scan, the time of arrival plays a secondary role in that it determines the distance of the image plane from the transducer; in a transmission C-scan, time plays no role whatsoever. A C-scan image resembles images obtained with x-ray fluoroscopy; hence, the images tend to look more familiar than a corresponding B-scan and are often more readily interpretable.

Because acoustic microscopes usually employ high-frequency acoustic waves, accurately-focusing lenses and high-precision mechanical scanning systems, the images taken have high accuracy. Using a computer, digital information obtained from tests using an acoustic microscope are digitized to save and display. In this manner, it is easy to observe the result. Also, an acoustic microscope can perform different functions, such as testing, observation and analysis using image processing and other signal processing techniques.

The conventional acoustic microscope contains four principal parts: pulse generation and signal detecting circuit 1, lens 3, mechanical scanning system 5, and also control and display 7 (FIG. 1). The pulse generation and signal detecting circuit 1 includes main pulse generator 9, pulse divider 11, high-frequency oscillator 13, amplifier 15, PIN modulator 17, circulator 19, matching network 21, amplifier and signal detector 23, pulse amplifier 25, sample and hold circuit 27, sample and hold pulse source 29, video frequency amplifier 31, filter 33 and pulse oscilloscope 35. The mechanical scanning system 5 comprises three-dimensionally adjustable workstation 37, XYZ axes moving and scanning. workstation 39, step-motor and position sensors 41. The control and display 7 comprises computer 43, keyboard 45, mouse (not shown), A/D interface board 47, parallel interface board 49 and monitor 51. The sample 53 is mounted on the three-dimensionally adjustable workstation 37 and is coupled to the lens 3 by a suitable coupling liquid 55, such as water.

Continuous microwave signals are generated by a microwave source (components 9 to 15) and pass through modulator where they are converted to modulated pulse signals. These signals go through circulator 19, matching network 21 and are converted to modulated acoustic pulses when they pass to the lens 3, and are focused by the lens 3 into the sample 53 and reflected from the inhomogeneous parts of the sample. Acoustic signals are reflected back to lens 3, through a transducer and converted to modulated electrical pulses. These pulses go through circulator 19, high frequency amplifier, then through detecting, amplifying, sampling and holding (components 23 to 33) to A/D converter 47, and are saved in the memory of computer 39 and displayed by the monitor 51.

Conventional acoustic microscopes have some important deficiencies:

1. The pulse time for gathering data is fixed, so only one section image is obtained for each scan (i.e. the plane perpendicular to the direction of travel of the acoustic waves). Each time one C scan image is obtained only. It is not possible to obtain C scan image of several cross-sections simultaneously.
2. It is not possible to obtain the structure of the plane containing the acoustic wave, i.e. the B scan and of course not possible to have A scan information. Hence it is very difficult to obtain a three-dimensional image.

In 1994, the applicant designed a multi-purpose imaging system that can obtain A, B and C scan images at the same time (FIG. 2). The inspection principle is similar to that described in relation to FIG. 1, and like elements are designated with the same reference numerals. The only significant difference is that, when above the specimen (X1, Y1) position, the lens sends a series of acoustic pulses to the specimen, and at the same time sends a series of data gathering pulses, the delay times of each of data gathering pulses relative to main pulses varying from small to large. Provided that each delay time between each data gathering pulse and main pulse is small enough, the series of data gathering pulses can be detected from the amplitude of reflected signals for a given point at different depths. By collecting all the reflected acoustic signals, an A scan image for this point (X1, Y1) is obtained. If the collected signals are used to modulate the brilliance of various points on this line, a B scan image is obtained. After the scan of XY surface of the sample is completed, all necessary information is obtained for internal three-dimensional structure, and hence a complete three-dimensional image is formed. This test system is an obvious improvement compared with the system shown in FIG. 1, because it can obtain A, B and C scan images, and internal three-dimensional structure for the specimen. The main disadvantage is that the speed is too low. It takes more than one hour to get a series of three-dimensional data.

In order to improve the scanning accuracy of the scanning acoustic microscope (SAM), Professor Kino of Stanford University, devised the system described in U.S. Pat. No. 4,503,708 (Reflection Acoustic Microscope for Precision Differential Phase Image)—see FIG. 3. The working process of the system of the U.S. patent is similar to the applicant's proposal described above. The difference is that, in the U.S. patent, not the amplitude but the phase of the reflected acoustic signals is measured. Here special hardware (lock-in amplifier and phase detector) are used to test the phase of reflected acoustic signals. The advantage of this system is high accuracy. It can examine the changing of depth for the membrane. The accuracy can reach about 10 angstrom. But this system is. much more complex than the system in FIG. 1. It is expensive and difficult to operate.

Another prior system is disclosed in U.S. Pat. No. 4,577,504 (Hitachi).

An object of the present invention is to mitigate the deficiencies of the four prior systems mentioned above. The system of the present invention may quickly obtain A, B, C scan images and display a three-dimensional image. The system may perform phase testing and imaging. Also the noise can be reduced. The system may obtain the internal character of the sample and differentiate with the model. The hardware may be very simple, only including the basic elements of the previous SAM for the collection of the original data and processing with software.

The present invention is defined in claims 1, 11, 12, 13 and 15.

For a better understanding of the present invention, an embodiment will now be described, by way of example, with reference to the accompanying drawings, in which.

Figure 1:
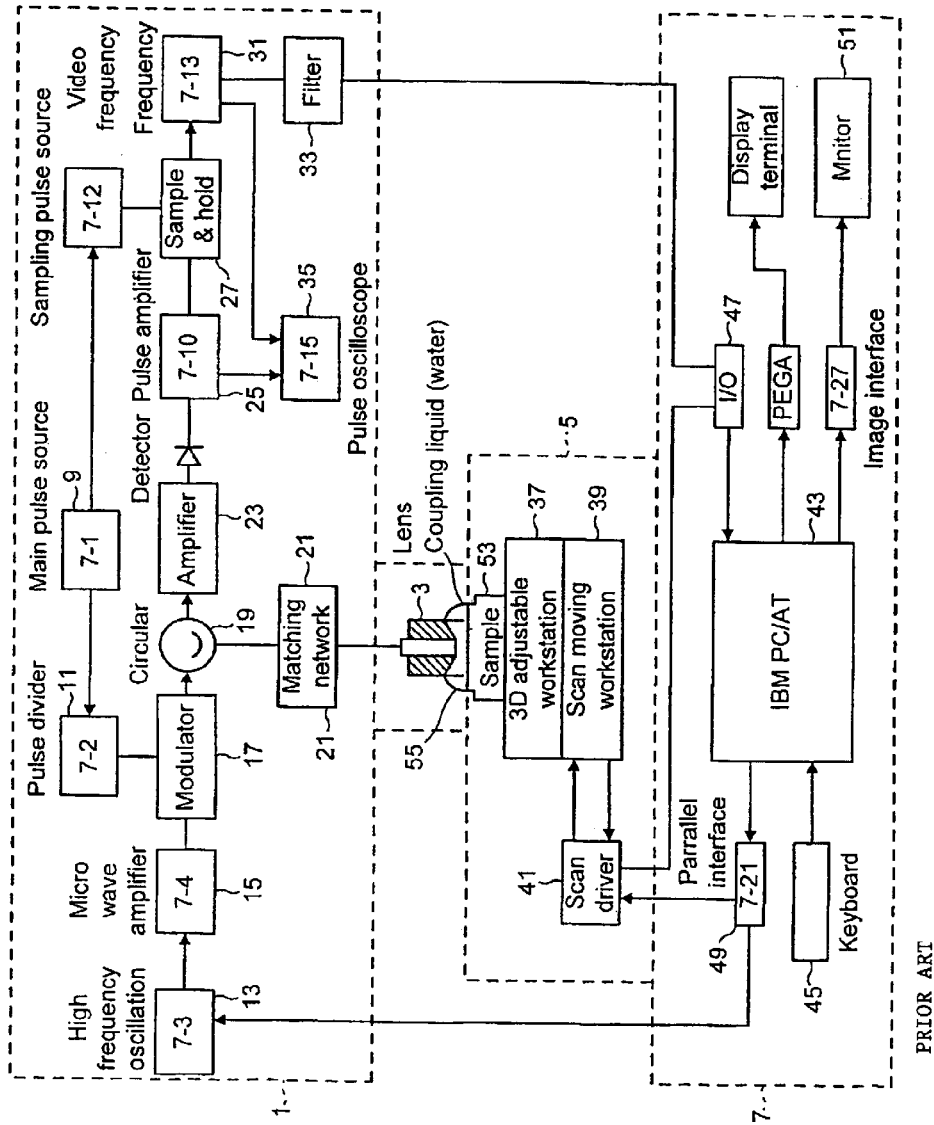
FIG. 1 is a block diagram of the main structure of a conventional SAM.
Figure 2:
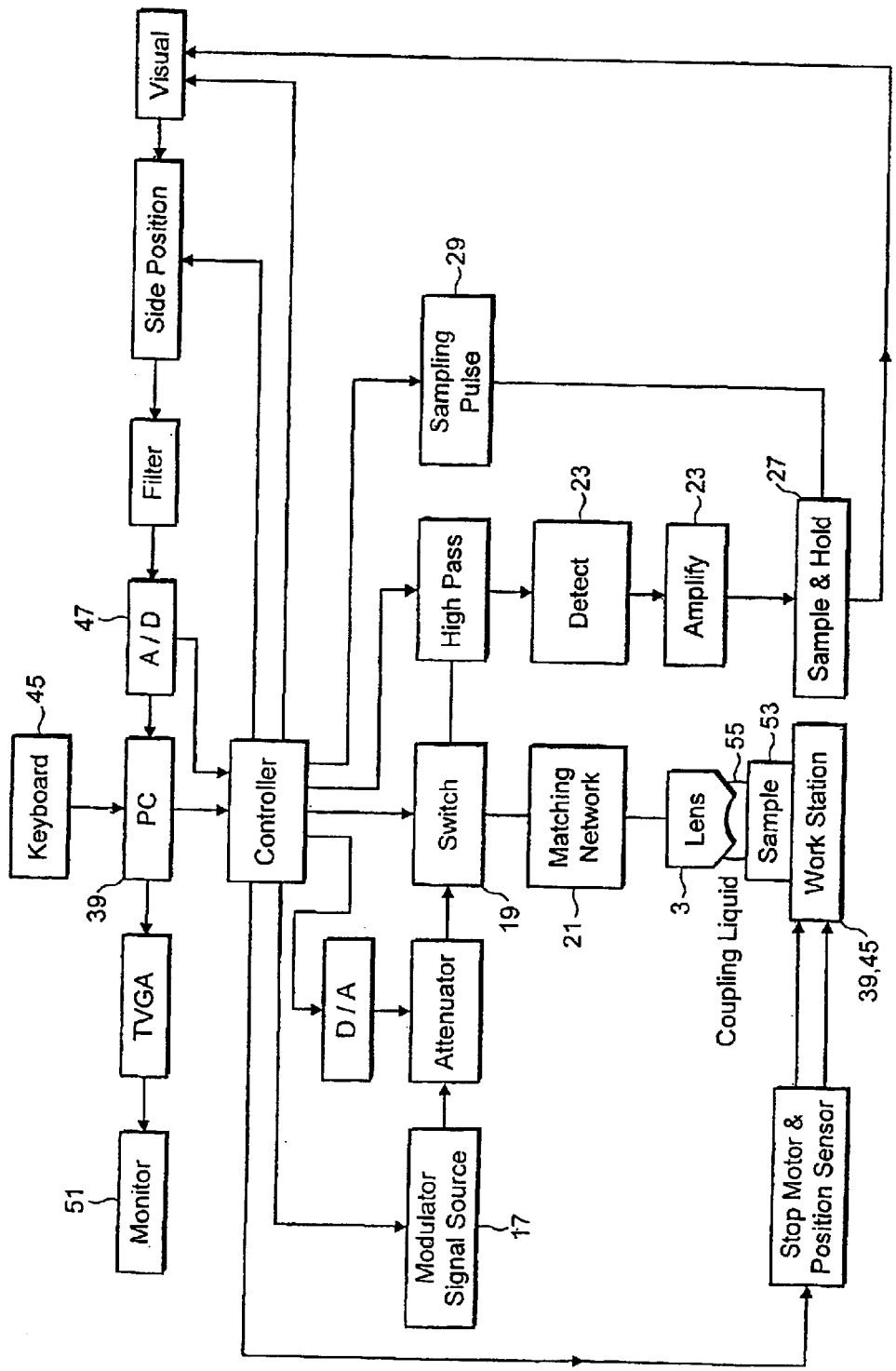
FIG. 2 is a block diagram of a prior SAM of the present applicant.
Figure 3:
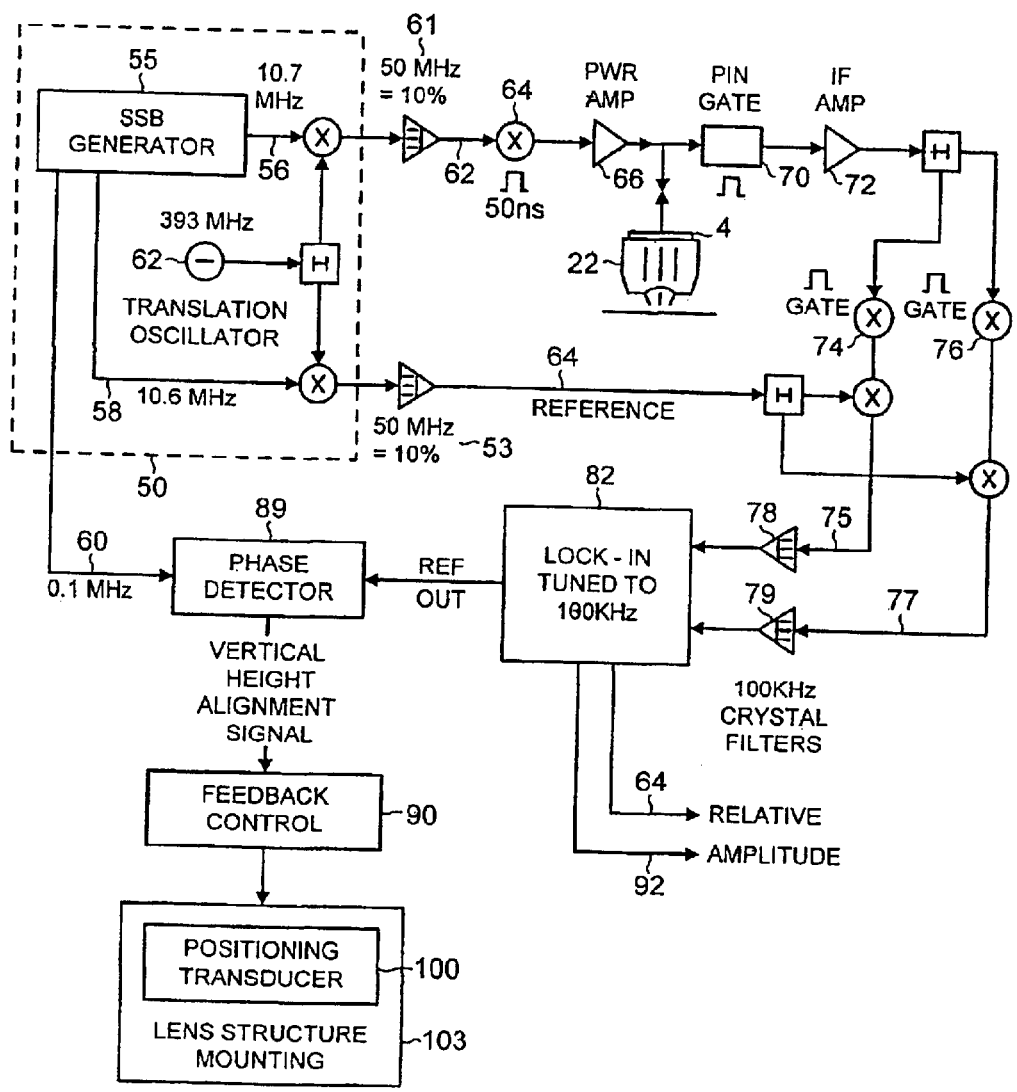
Figure 4:
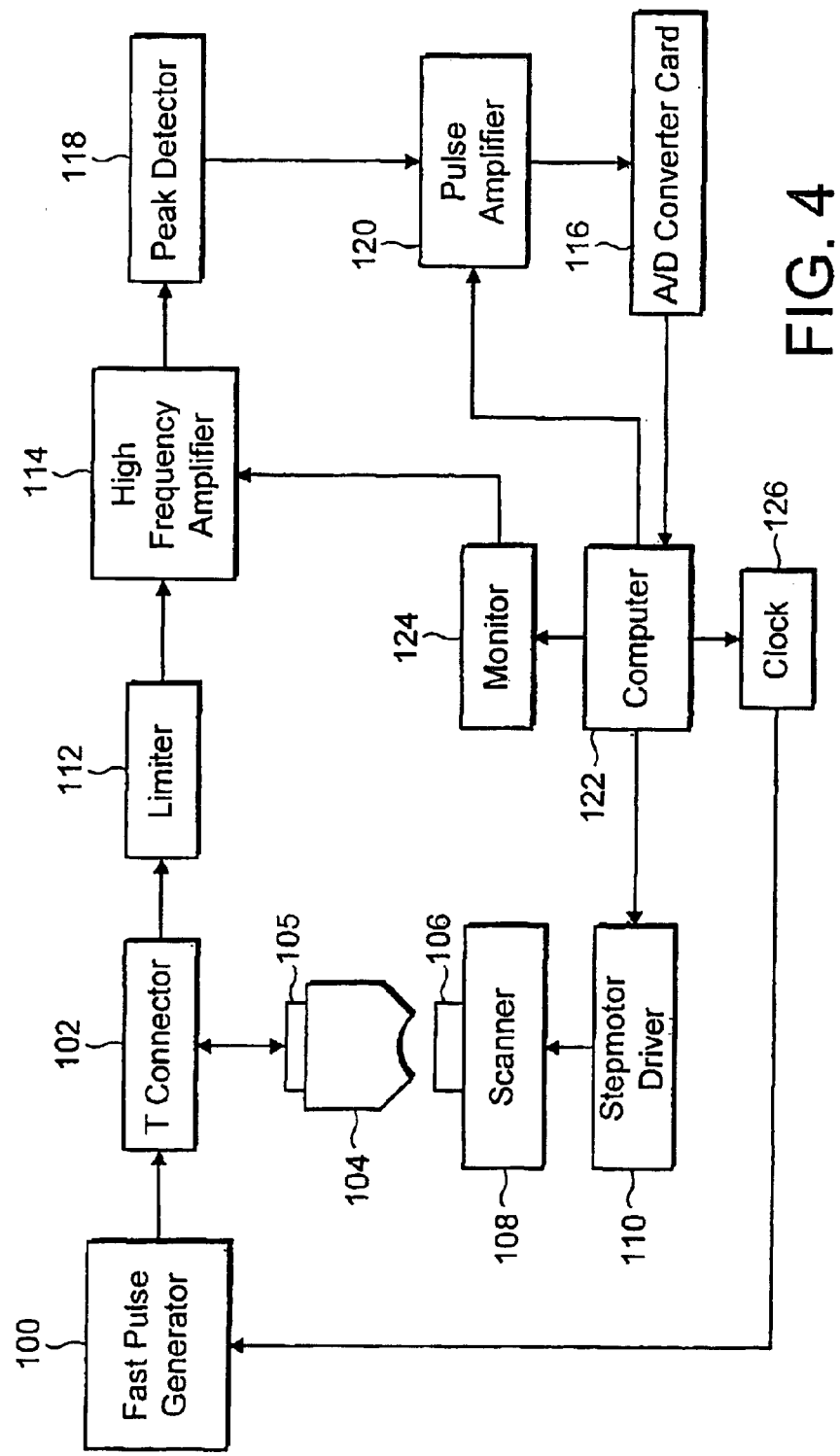
Figure 5A:
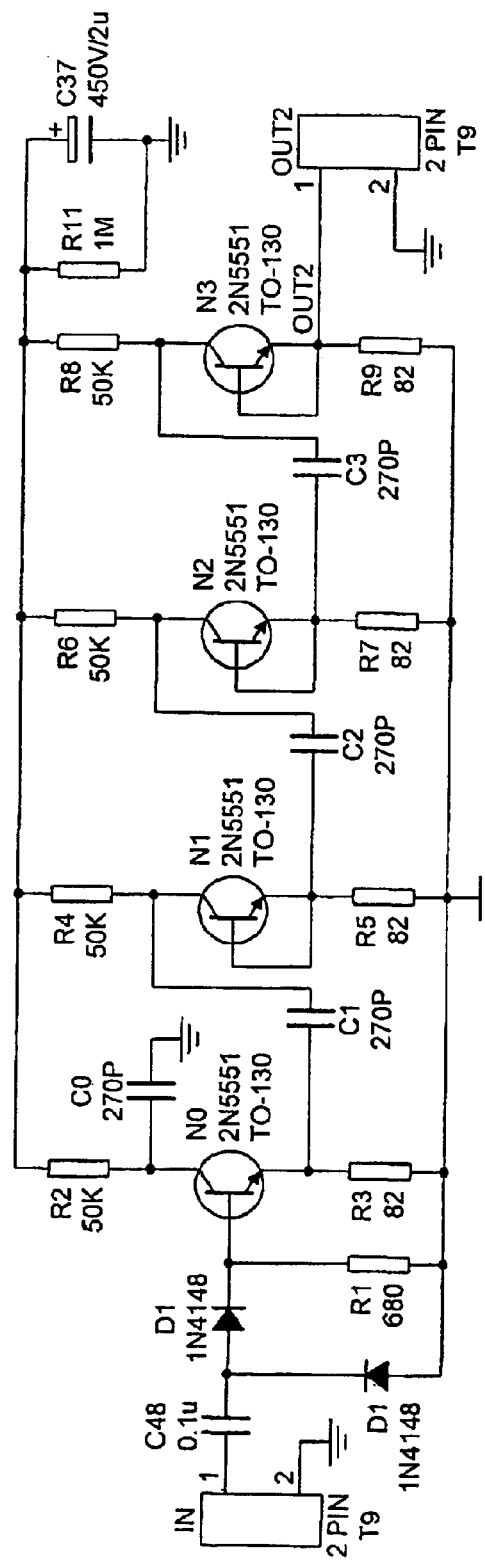
Figure 5B:
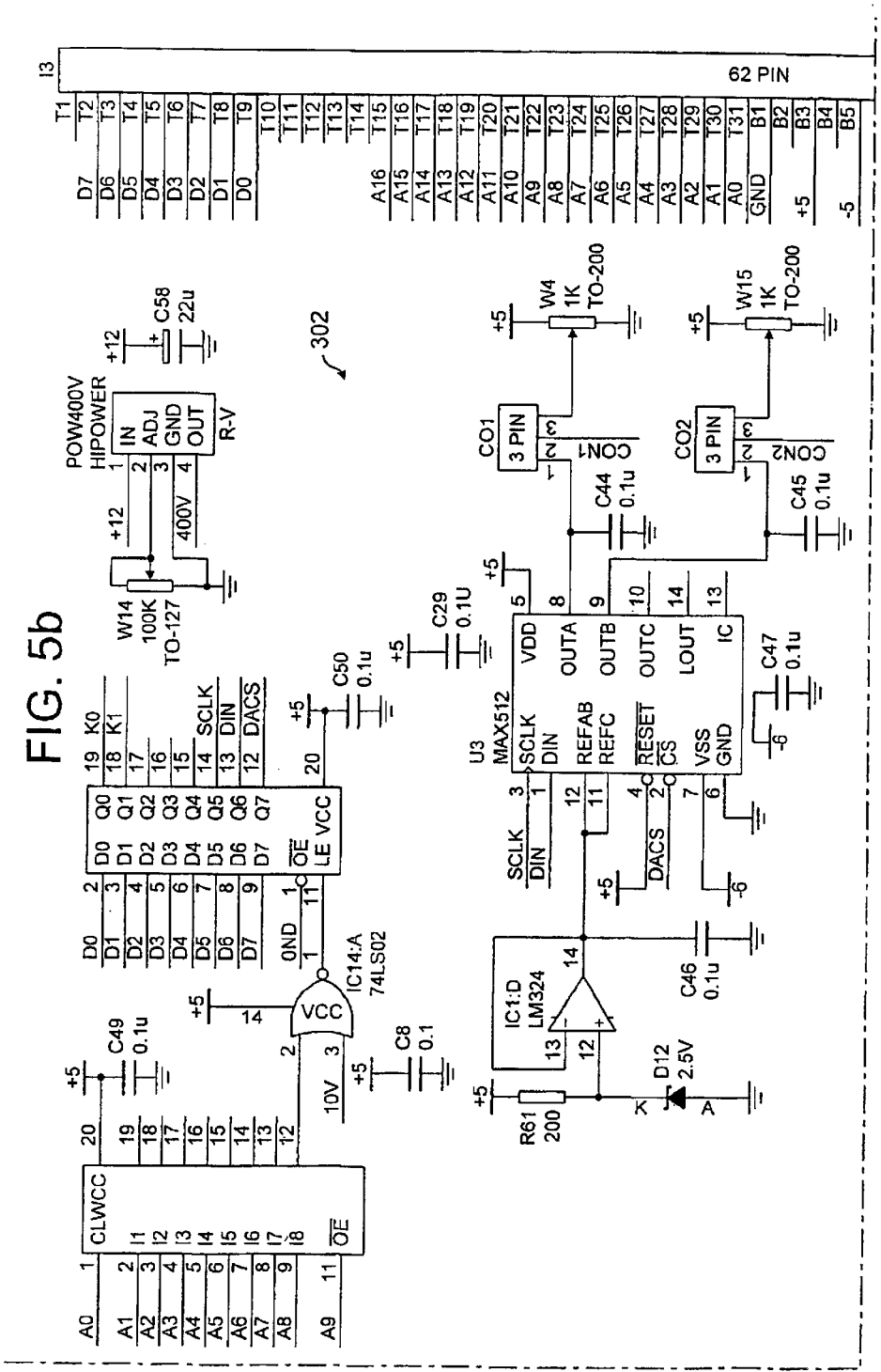
Figure 5C:
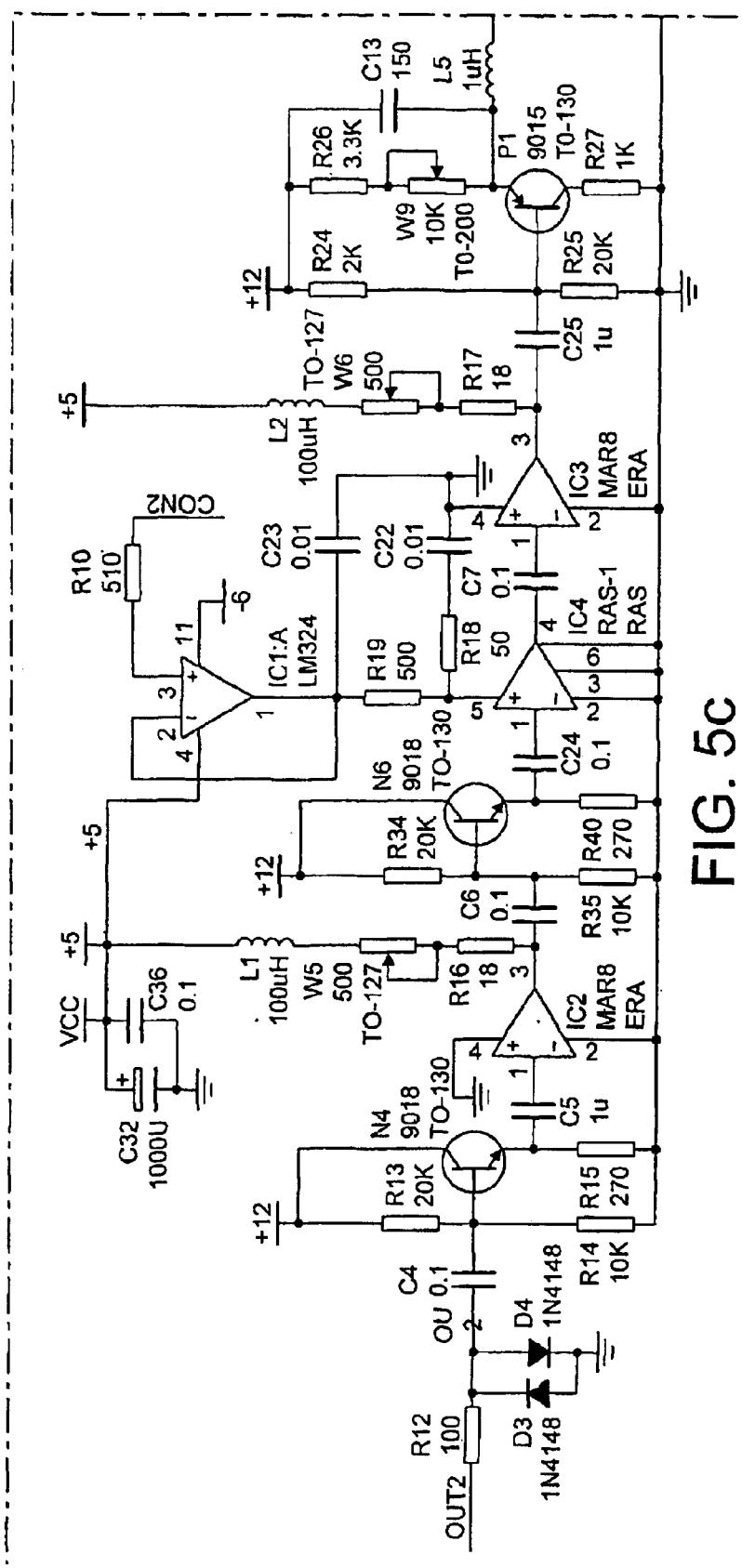
Figure 5D:
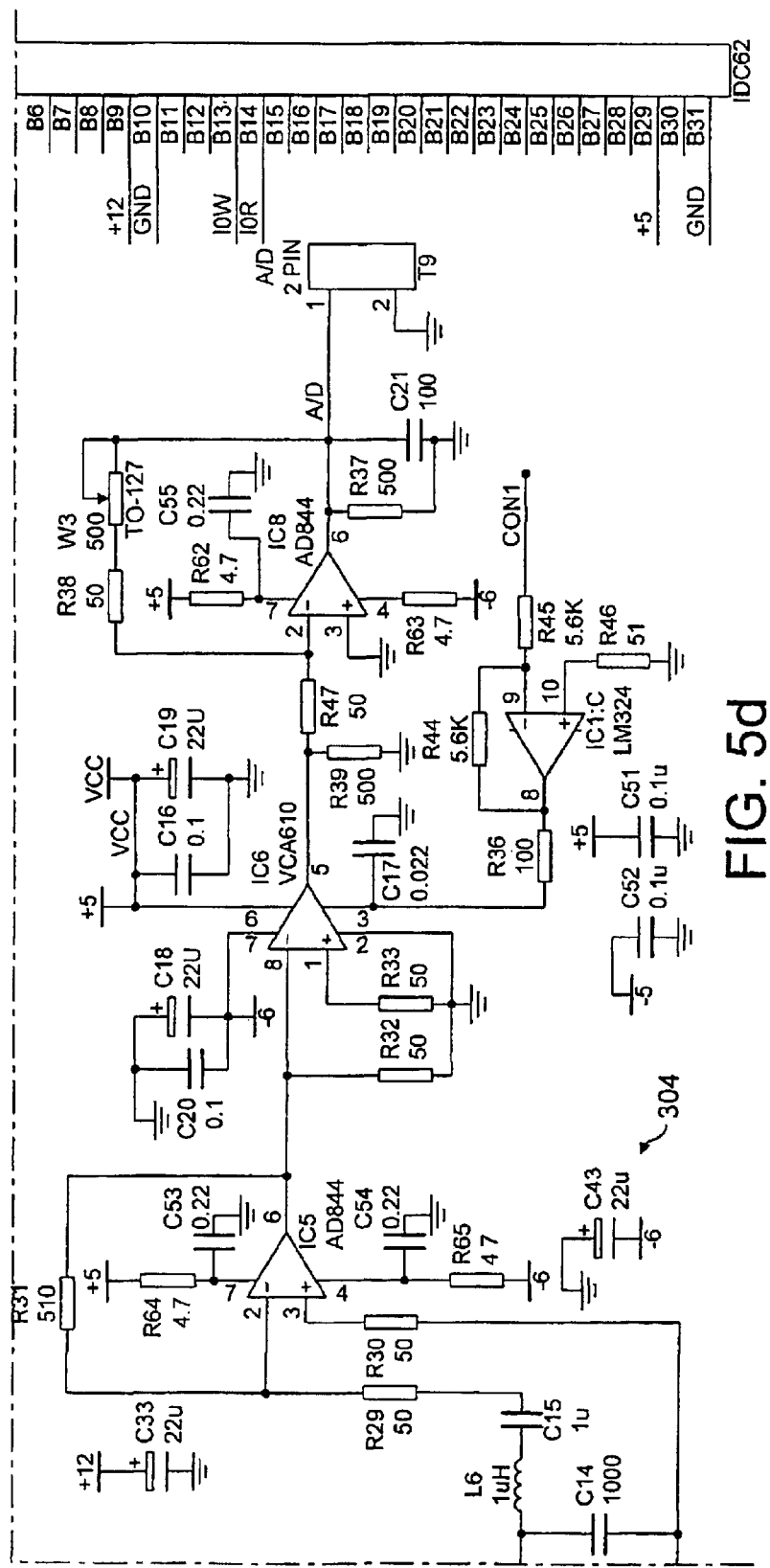
Figure 6:
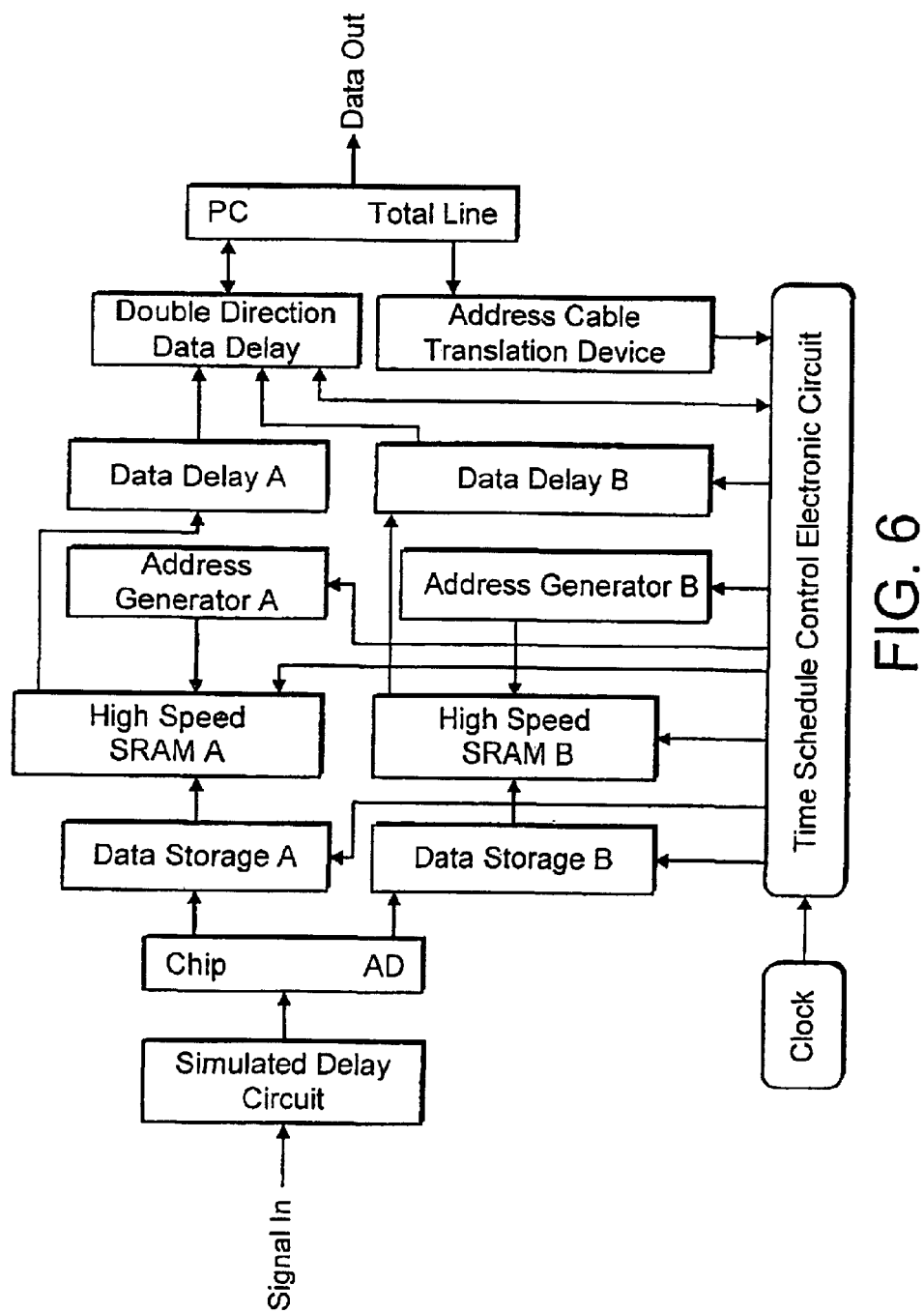
Figure 7:
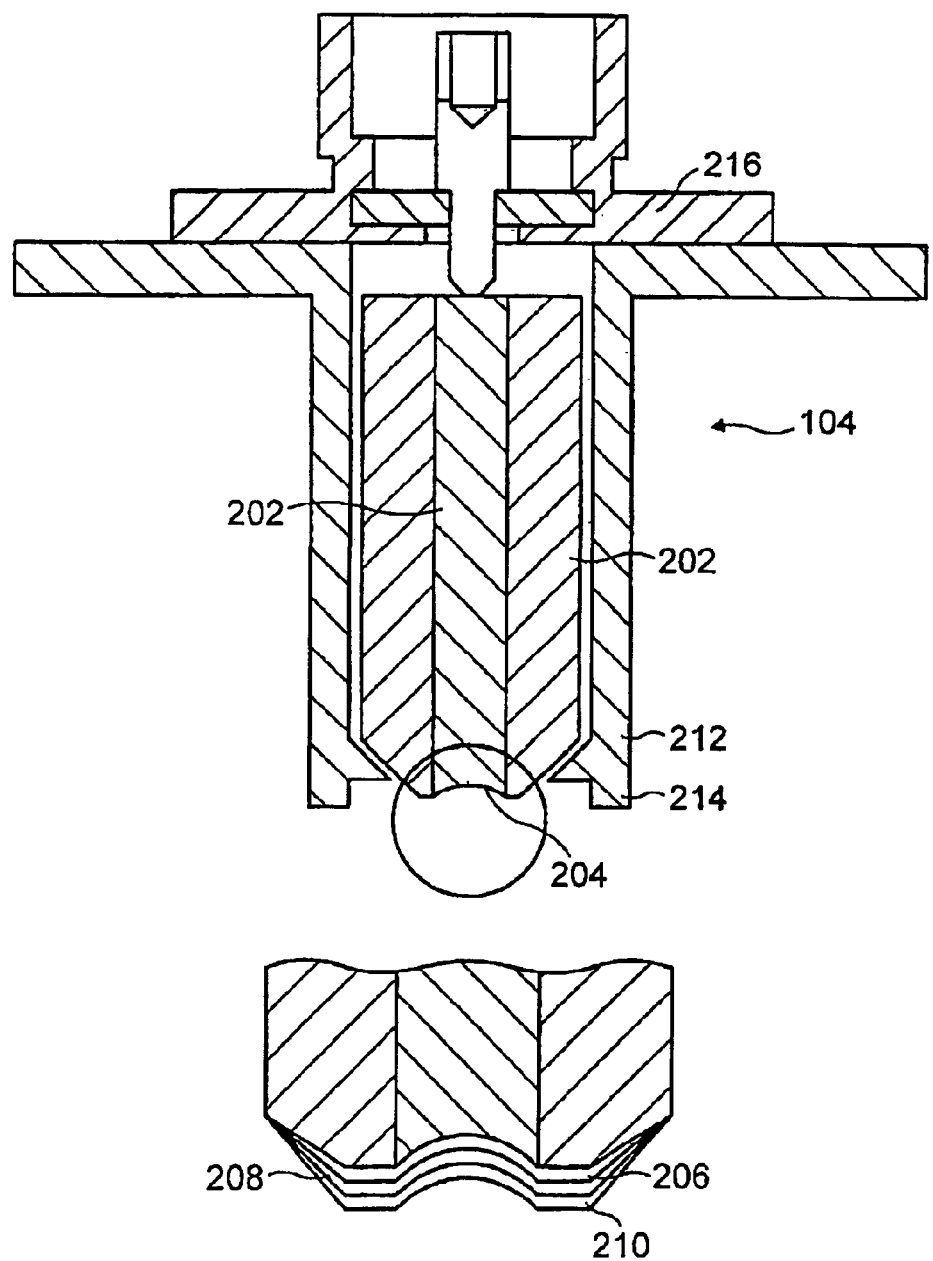
Figure 9:
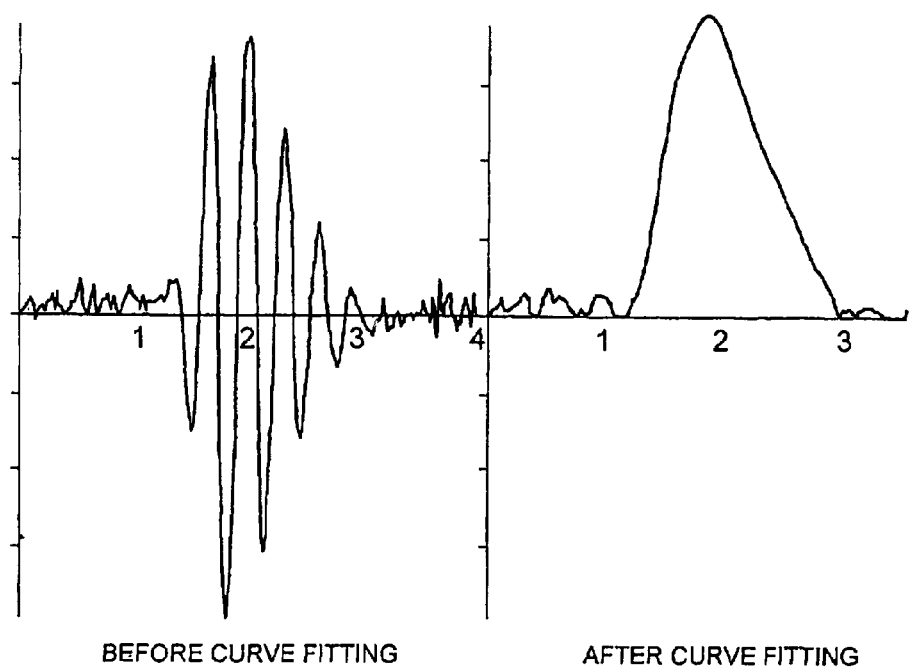
Figure 10:
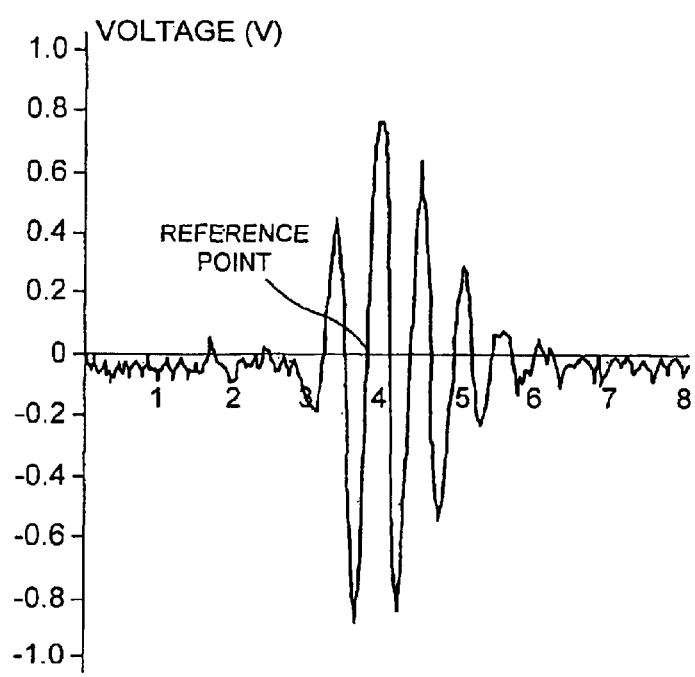
Figure 11:
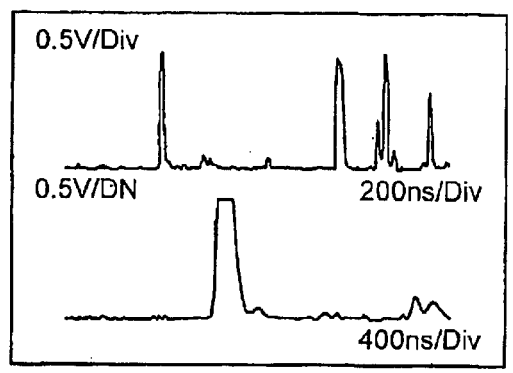
Figure 12:
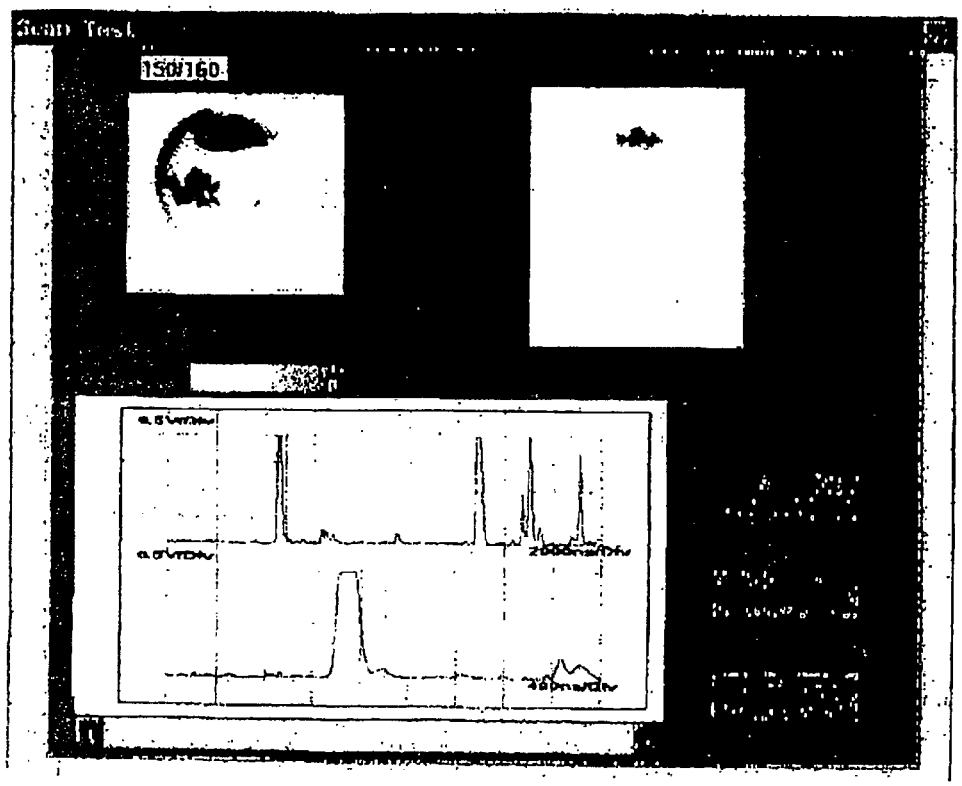
Figure 18:
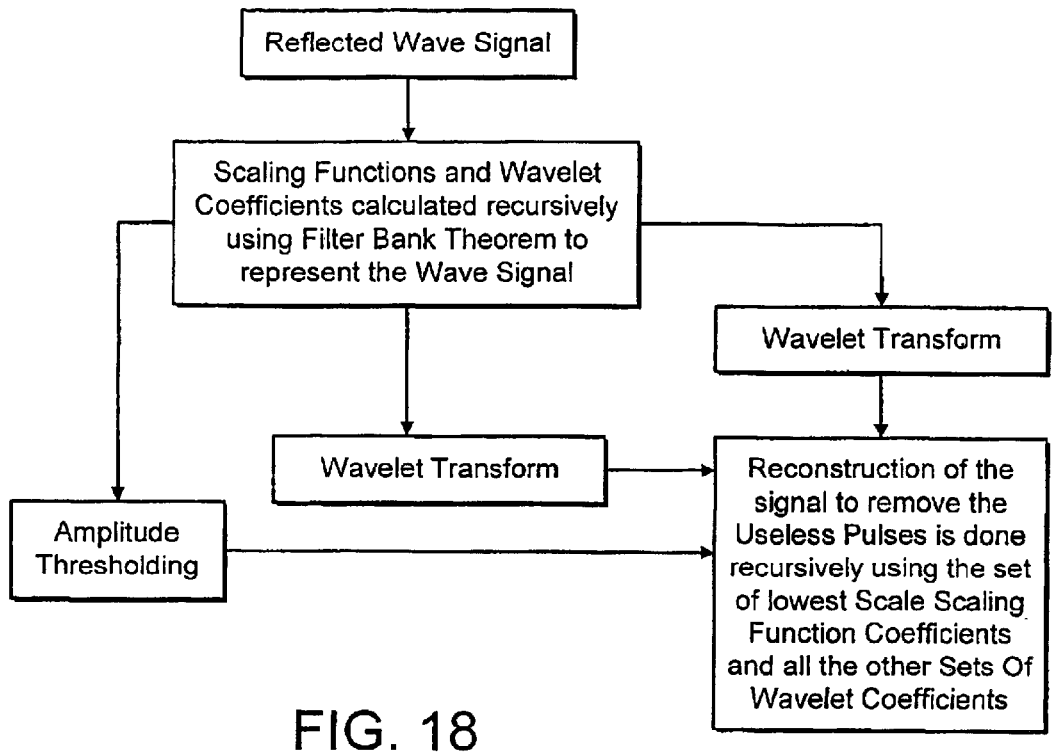
Figure 19:
Figure 20:
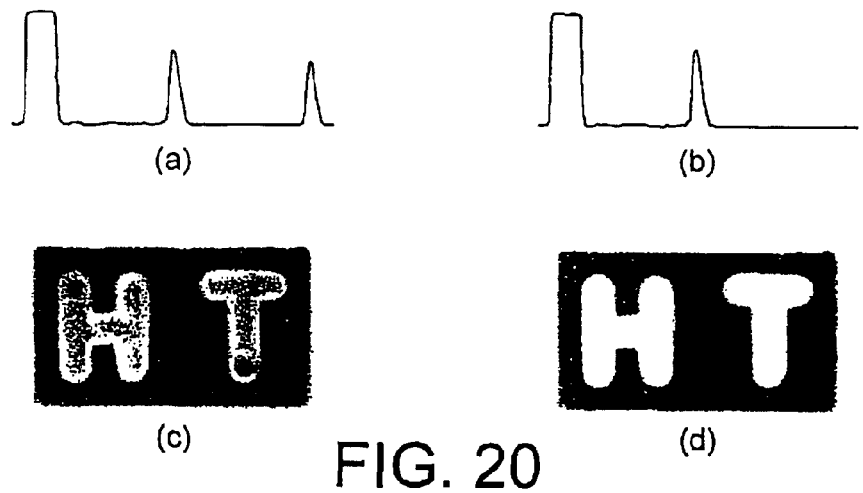
Figure 21:
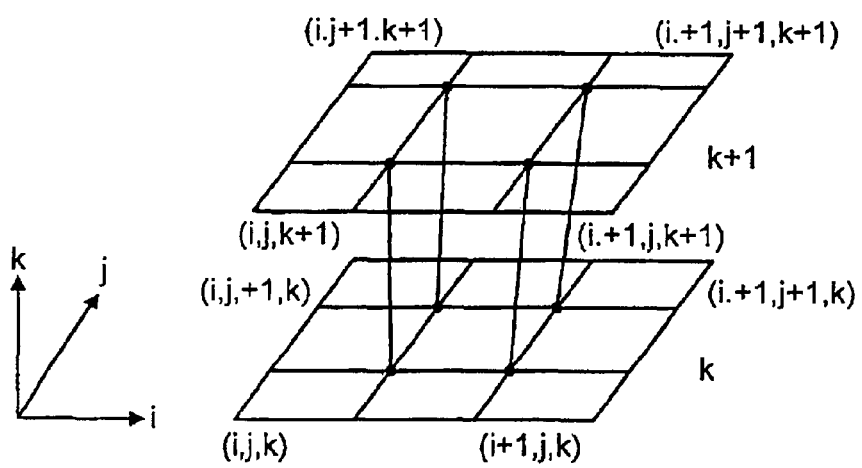
Figure 22:
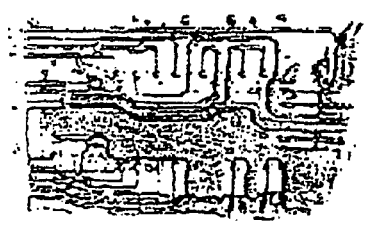

FIG. 3 is a block diagram of the prior SAM of U.S. Pat. No. 4,503,708;

FIG. 4 is a block diagram of the present invention;

FIG. 5 is a circuit diagram of the pulse generator/receiver;

FIG. 6 is a block diagram of the A/D converter;

FIG. 7 is a cross-sectional view through an acoustic lens;

FIG. 8 shows the processing of the reflected waveform;

FIG. 9 is a schematic showing the theory of curve fitting;

FIG. 10 is a schematic showing the theory of phase testing;

FIG. 11 shows an A scan waveform;

FIG. 12 shows A, B, C scan images;

FIGS. 13, 14, 15 and 16 show example C scan images;

FIG. 17 shows the elimination of a fixed pulse from an A scan waveform;

FIG. 18 is a flow chart showing the removal of useless fixed pulses;

FIG. 19 shows the reduction in pulse width of an A scan waveform;

FIG. 20 shows the elimination of the multireflections from A and C scan waveforms;

FIG. 21 illustrates the cubic voxel in the Marching Cube Algorithm;

FIG. 22 shows an image of the internal structure of a flipchip;

FIG. 23 shows an image of the bottom surface of a ceramic plate;

FIG. 24 shows an image of the interior delamination of the structure shown in FIG. 12(c);

FIG. 25 shows images of the interior structure of an aluminum sample; and

FIG. 26 shows the software frame of the invention.

The principal components of the acoustic microscope are shown schematically in FIG. 4. A pulse generator 100 produces high speed and high voltage pulses. The output of the pulse generator 100, which will be a series of 400 V, 10 ns duration pulses, is applied to T connector 102. Electrical pulses are sent from the T connector 102 to an acoustic lens 104, under which a sample 106 is located. A transducer 105 is mounted on the lens 104. For frequencies higher than 10 Mz, the transducer is ground from 36° Y cut $LiNbO_3$ single crystal. For frequencies lower than 10 MHz, the transducer is made from PZT piezoelectric ceramics. A liquid (not shown) couples the lens 104 to the sample 106. The coupling liquid is typically distilled water. The sample 106 is mounted on a scanner 108, which is moved by stepmotor driver 110. The sample can be moved along three perpendicular (XYZ) axes.

The SAM uses a multidimension adjustment structure. It has two sets of angle adjusters, separately mounted on the transducer support, and the sample stage. At the transducer support, there is a focus adjuster. The horizontal scanning of sample by the ultrasonic wave bundle is achieved by a mechanical method. The grating style scanning of the sample is achieved by using a PC to control the step motor to drive the high precision moving stage. Due to the broad frequency range of the system there is a big difference in the sensitivity requirement. Ad low frequencies, the step motor 110 moves in steps of three beats. But at high frequencies, the step motor 110 moves in more minute intermediate steps.

The pulse excites the lens 104 and generates an acoustic wave with a frequency of 25–200 MHz that is incident on the sample 106. Due to inhomogenities in the sample 106, acoustic waves are reflected back to the lens 106. The reflected waves are converted into electrical signals and pass from the T connector 102 to pulse limiter 112, thence to high-frequency, high-gain amplifier 114. The electrical signals generated by the lens will comprise a series of high-frequency modulated pulses.

Components 100, 102, 112, 114, 118 and 120 comprise a pulse generator/receiver. The pulse generator/receiver may be in the form of a PC card. The pulse generator/receiver has a simple structure with a direct current high voltage electrical source and a high quality Marx type avalanche electronic circuit.

The output of the amplifier 114 of the pulse generator/receiver passes to A/D converter 116 via peak detector 118 and pulse amplifier 120. The A/D converter is in the form of a PC card, and is a high speed device with a sampling rate of over 1 GSPS and a differentiation rate of 8 bits. It can digitize un-modulated signals with frequencies above 100 MHz. The digitized output passes to computer 122, such as a PC with PII 300 MHz processor.

The ultrahigh speed A/D digitises the reflected wave signal and allows the software to carry out signal processing and display functions. It satisfies the requirement of real-time. acquisition. The principles of the ultrahigh speed A/D card are given in block diagram as follows in FIG. 5. The integrated circuit chosen for the A/D card is the AD9058, which has a speed of 50 MSPS. The AD9058 has parallel processing characteristics, and the opposite phase function is employed to increase speed to 100 MSPS. An equal time multiple phase acquisition technique is used. Software controls an AD9501 integrated circuit to produce a series of delayed pulses. Multiple data acquisitions replace a single data acquisition. Therefore, the actual data acquisition speed is the single data acquisition speed multiplied by the number of times data is acquired.

The computer 122 runs software for interpreting the signals reflected from the sample 106. The results are displayed on monitor 124. A clock signal generator 126 synchronises the computer 122, the pulse generator 100 and the A/D converter 116. The computer 122 controls the stepmotor driver 110 and scanner 108 using its parallel output part.

The computer 122 has control of the overall system shown in FIG. 4. The software run by the computer replaces many of the hardware components of the prior art described above. This reduces the cost and size of the system, whilst allowing additional functions to be provided. The only functions performed by hardware are essentially signal generating, amplifying and digitizing.

A circuit diagram of the pulse generator/receiver is shown in FIG. 5. The pulse generator/receiver comprises a Marx type avalanche circuit 300 including four 2N5551 transistors. This avalanche circuit is commercially available. Control circuits 302 which control the initial functions and increase the performance of the pulse generator/receiver are also provided. Receiver and amplifier stage 304 receives and amplifies the sound wave signal resulting from reflection of sound waves from the acoustic lens 104. The output of the stage 304 is prepared for transmission to the A/D converter 116. Software running of the computer 122 supplements the functions performed by the circuitry shown in FIG. 5, and this allows the circuitry to be simpler than that which is conventionally employed.

The acoustic lens 103 is a glass and metallic ball surface transducer type acoustic lens. The structure of the lens is shown in FIG. 7, which is a cross-sectional view. The lens comprises a molybdenum rod 200 surrounded by glass 202. The glass and metal may be intermelted and intersealed. The part of the lens 104 which is nearest the specimen 106, in use, has an indentation 204 corresponding in shape to part of a sphere. On the lower surface of the lens 104, including the indentation 204, a piezoelectric layer 206 is formed. The layer 206 may be of zinc, oxide, lithium niobate or silica. A metallic, for example gold, film 208 is formed over the piezoelectric layer 206. The layers 206 and 208 comprise an electrode. outer protective layer 210 is then formed over film 208. The protective layer 210 is a high-hardness, grinding resistant film, such as silicon nitrate or granite formed by a MPCVD technique.

The assembly described in the preceding paragraph is located in a housing 212 formed of, for example, copper. The housing may include downwardly-extending claws 214 which extend beyond the lower surface of the assembly to protect the assembly in case of contact with the specimen 106 or any other object. The copper of the housing 212 may be joined with the gold of the film 208 to form the electrode.

A coaxial connecting socket protects the upper surface of the lens.

The diameter of the rod 200 is less than the diameter of the indentation 204. The sound wave produced by the lens 104 is a spherical wave and will be convergent and will not produce interference waves. Compared with a sapphire flat surface transducer type acoustic lens, there is one less reflection surface so losses are reduced. Also, because the materials used are much cheaper, the cost of the lens is significantly reduced. The glass/metal structure is relatively easily damaged, but this disadvantage is mitigated by the provision of the protective layer 210 and the claws 214.

The functions performed by the acoustic microscope can be summarised as follows:

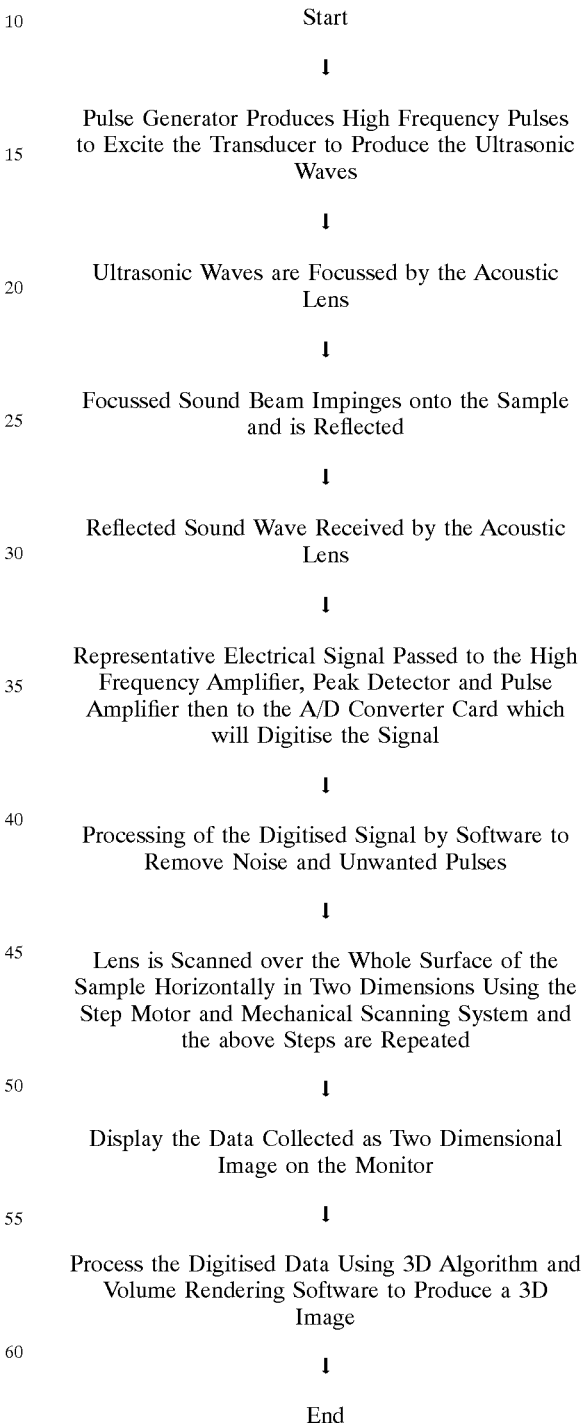

To analyse a sample, the sample 106 is moved so that the lens 104 is centred over a particular point (coordinate value X, Y). The PC controls the A/D card to send out an excitation signal. It excites the electronic circuit to produce 300 V high speed pulse. This excites the acoustic lens to produce a high frequency ultrasonic beam. It will be reflected at the sample's interface or at the uneven part within the sample. The reflected wave will be received by the acoustic lens, and transformed into electrical signal (as shown in FIG. 8). After amplification, the reflected signal will be transmitted to the ultrahigh speed A/D card to be converted into a digital signal. Then the software will be used for processing to reduce noise and to carry out wave inspection and wave filtering.

The A/D card transmits a signal, which is reflected and has a waveform as shown in FIG. 8(a). Then the more effective wavelet transform method will be selected for noise reduction. With Mallat high speed computation, the result after noise reduction is shown in FIG. 8(b). Then the Akima method is used to carry out wave selection and wave filtering. The results are shown in FIG. 8(c). Using software for noise reduction, wave selection and wave filtering, can produce a better effect, reduce hardware and easily achieve ultrawide band wave filtering.

The signals after analysis are stored in the computer. It displays at the same time the A scan waveshape of the sample along its depth direction, and the B scan and C scan after processing. The software will excite the scanning mechanical system to move to the next point on the sample and repeat the above procedure.

Scanning will occur in the X direction. The lens is moved to the next position of the specimen with coordinate value X2Y1, and the analysing and storing steps are repeated. The sample then moves to X3Y1 . . . XnY1. After finishing scan of each line, the sample moves from Y1 to Y2, and then completes the Xn . . . X2 X1 scan. At each point the same testing, processing, saving and displaying steps occur. The process is repeated with scanning Y2 to Y3, and to Y4, Y5 . . . Ym. At each value of Y, X will scan for a line.

The phenonmenon of Rayleigh wave travel through a medium using a wave generated by an acoustic microscope is described in the report "Microwaves, Acoustics and Scanning Microscopy" by C. F. Quate, appearing in the Proceedings of the Rank Prize International Symposium on Scanned Image Microscopy.

The V(z) curve is applied, in the present embodiment to evaluate quantitative elastic properties of the specimen 106.

The computer 122 is programed to enable the automated measurement of the V(z) curve. Here the v refers to the video or envelope detected signal that is used to modulate the brightness of the image, and z refers to the amount by which the specimen surface is displaced from the focal plane of the lens. By convention the focal position is designated z=0, and displacement of the speciment away from the lens is taken as positive. The process of the decreasing the separation of the lens and speciment relative to the focal distance is often referred to as defocusing. The most interesting phenonmena occur at negative defocus and are closely related to the elastic properties of the specimen. The elastic property of the specimen can be determined by measuring the V(z) curve and using the relation $$V_R(z) = V_0 \left\{ 1 - \left[ 1 - \frac{V_0}{2f\Delta z} \right]^2 \right\}^{\frac{1}{2}}$$

Where $V_R$ is the Rayleigh wave speed, $V_0$ is the speed of the coupling fluid, f is the frequency and $\Delta z$ is the period of oscillations in the curve. The elastic properties of an isotropic specimen are completely characterized by two independent engineering elastic constants, namely E and υ, the Young's Modulus-and Poisson's ratio respectively. These two constants are related to the Rayleigh wave speed by the following equation.

$$E = 2(1+\upsilon)\rho_R^2 \left[ \frac{1+\upsilon}{0.87+1.12\upsilon} \right]^2$$

Where ρ is the density of the specimen. Thus, the Young's Modulus of the specimen can be determined by measuring $V_R$ if the density and the Poisson's ratio are Known.

A Fast Fourier Transform is performed on the measured V(z) data to obtain data z. The program is written in Matlab. From a discrete amplitude plot, data z can be obtained.

To perform V(z) curve testing, the lens 104 is located above certain position XY of the specimen 106. The Z value, the distance between lens and specimen, is adjusted to an expected value, electrical pulses are initiated, reflected acoustic signals are tested and saved into memory. By multiplying the phase time differences between the specimen surface and reflected signals of lens surface, both of which have the same phase with sound velocity in water, then Z, the distance between the surface and lens, is obtained. The maximum value of V1 is obtained from testing the reflected acoustic signals. Using Z as horizontal coordinate and V as vertical coordinate, point V1Z1 is plotted the lens scanned in Z direction. The distance between the lens and specimen is changed to Z2. The same method as before is used to test reflected voltage value V2 at point Z2. Point Z2V2 is then plotted. The drive lens is then again scanned in Z direction to Z3. V3 is obtained. This procedure is repeated until the lens moves to Zn, and voltage value Vn is obtained. Then on the monitor of computer a V(z) curve is plotted. In the computer memory, pairs of V(z) data are saved. Then V(z) analysis software is initiated.

To obtain depth information for each point on the is sample the maximum value of the signal and the corresponding time coordinate at which it occurs are determined. The software applied curve fitting to obtain a smooth curve using the maximum point curve fitted, and displays the curve on the monitor (FIG. 9). This is the detecting wave of reflected signals, also called normal A scan image. With this data B and C scan images are formed.

When phase information of the sample is needed, reflected acoustic waves carrying signals gathered above are used, taking certain periods of certain layer generating acoustic waves as reference, to calculate the chase difference from the same period another layer generating reflected acoustic waves, and then obtain the phase image for this layer (FIG. 10).

When model identification or low noise is needed, a method, such as wavelet transform or a neural network, is used to reduce the noise or identification model for the reflected waves carrying signals gathered above When this has been completed the A, B and C scans will be displayed, the C scan image showing depth of the specimen. Original acoustic waves, processed pulse width and phase information of all points of internal three-dimensional structure are saved in the memory of the computer. This information mast be used for further processing, completing model identification and three-dimensional imaging. The results will display on the monitor with manuscript, data or images, or save in disk, CD or can be printed out.

Similar to any scanning image formation system, the image formation procedure is based on the convolution of the objective function and the point spread function of the image formation system. Due to the fact that we are aiming at 3D image formation, the SAM's image formation equation is as follows:

$$U_d\left(\frac{x_d}{M}, \frac{y_d}{M}, \frac{z_d}{M}\right) = \int\int\int_v^h (x_0, y_0, z_0) R(x_3 - x_0, y_3 - y_0, z_3 - z_0) dx_0 dy_0 dz_0$$

Where
h=point spread function of image formation system,
R=sample's reflection coefficient.

The above equation is different from ordinary image formation equation. The usual equation only considers the 2D scan of the probe along the sample's surface and treats image formation process as the 2D convolution of the objective function and the image system's point spread function. In reality the acoustic lens not only has 2D aberration in the horizontal direction, in the depth direction also exists the effect of pulse spread due to reaction from the electrical system pulse. This is also a type of aberration. That is, in reality, the system possesses a 3D aberration. Hence the system point spread function is a 3D function. The image formation equation is the 3D convolution of the 3D point spread function and the objective function. During A scanning, the independent variables $X_0$, $Y_0$ are automatically cancelled, the voltage sent from the transducer will be the one D convolution of the sample's reflected function along the depth and the pulse reaction of the inspection electrical circuit. During B scanning, one of the independent variables of $X_0$, $Y_0$ (e.g. $X_0$) will be automatically cancelled. The output of the transducer output along time (or along z) and y will be the 2D convolution of the pulse reaction of the inspection electronic circuit and the 2D point spread function $h(y_0, z_0)$ formed by the aberration of the acoustic lens along the y direction. During C scanning, the independent variable $z_0$ is automatically cancelled. The distribution source of the transducer output along $X_0$, $Y_0$ is the convolution of the point spread function $h(X_0, Y_0)$ formed by the aberration of the acoustic lens along the $(X_0 \ Y_0)$ direction and the objective reflection function. During 3D image formation, the independent variables $X_0 \ Y_0 \ Z_0$ all exist. The spatial distribution of the transducer output is the resulting 3D convolution of the 3D point spread function in the broader sense $h(X_0, Y_0, Z_0)$ and the objective function $R(X_s, Y_s, Z_s)$. Beside this, the multiple reflection of the sound wave during measurement and the regular reflections caused by the existence of the non working model of the lenses also have important influences on the image formation.

The above analysis is the theoretical basis of the research in 3D image formation. It is pointed out here that in general ultrasonic inspection applies to the interior of the samples. The point spread function not only depends on the frequency, but is also related to the transducer structure, type of coupling liquid, sample material, shape of the sample and its depth.

In the present system, the scanning of the ultrasound beam along the x, y direction is accomplished by mechanical scanning. The z axis scanning is accomplished using scanning from the accumulation of time. In order to obtain sufficient accurate data acquisition, one needs to satisfy sample acquisition theorem. To enable the results of data acquisition to be close to reality, one needs as many acquisition points as possible. That is, the data sampling rate of the A/D card must be as high as possible. This will enable the waveform recovered after digitisation to be as close to the waveform of the original signal. According to the sampling theorem, acquisition time interval $\Delta t \pm \leq \frac{1}{2}$ fn, fh is the portion of the highest frequency among the acquired signals or A/D card acquisition sampling rate fs $=1/\Delta t \geq 2$ fn. In the applicant's experience, in order to obtain an accurate waveform one needs fs$\geq$10fh. The A/D card acquisition sampling rate is fs$\geq$1GSPS. Hence it is able to perform accurate acquisition of ultrasound signals above 100 MHz.

During even higher acquisition rate to acquire data, the data acquired will occupy greater storage space, and reeds longer processing time. Fortunately, the computation speed, storage and software level has been continuously increasing By way or example, sample inspections will now be described.

During the sample inspection, one places the sample onto the sample stage and adds the couplant. Then the PC and software are initialised. The inspection frequency, scanning limit, speed and acquisition depth are selected. When the inspection has started, the computer display will show the A scan waveform. Also one can enlarge any required section of the waveform to see the details. The A scan waveform shown on the PC display is given in FIG. 11.

During the inspection, the A scan waveform and typical data will be shown at the lower part of the PC monitor display (FIG. 12). The upper right portion of the PC display will show the B scan image and the upper left portion will display the C scan image. The typical results are shown below.

Figure 13:
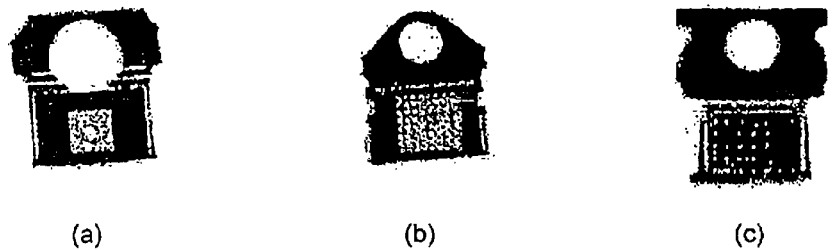

FIG. 13 shows the C scan image of the internal structure of the three power triode tubes.

Figure 14:
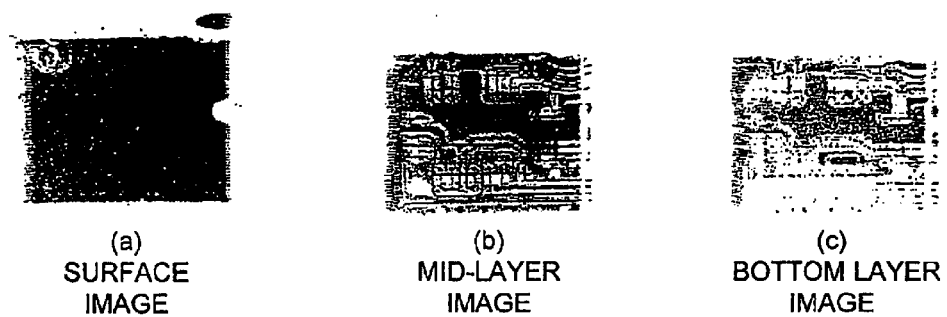

FIG. 14 shows C scan images of Flip Chip's multi-layers at different depths.

Figure 15:

FIG. 15 shows C scan images of the bottom layer structure of the metallic ceramic base plate.

FIG. 16 shows C scan images of the ceramic metallic welding structures of the three different samples. The sample after dissection confirms that the above images are correct and of high precision. The images show that the system can also inspect nonflat surface samples.

The software for SAM's 3D data visualization can be divided into three modules: preprocessing of data, projection, and drawing and display.

1. Preprocessing Data

After standardising the data, one follows a fixed format to store them, and performs preprocessing on these data. According to the image formation of SAM, one needs to perform the following preprocessing steps before the projection transformation.

a. Elimination of Fixed Pulse

The acoustic lens after high speed pulse excitation will produce a series of useless fixed pulses mixed within the reflected wave signal. This fixed pulse has to be eliminated during data preprocessing. FIG. 17(a) shows the useless fixed pulse of the lens and FIG. 17(b) is the A scan waveform that includes the useless pulse. The A scan waveform after the elimination of the useless pulse is shown in FIG. 17(c).

The technique of wavelet transform is used to eliminate the useless fixed pulses. As the specimen is raster scanned, all the readings can be arranged into a straight line and a one D wavelet transform performed on them. To do this the readings acquired from the SAN have to be stored in the computer's memory first. After which wavelet transform and denoising will then be performed on them. The program performs one D wavelet transform, amplitude thresholding and reconstruction is written suing a C++ compiler. In this program, the Haar scaling function and wavelet are used.

Their scaling coefficients formed the respective filter banks. The signal samples are used as the first set of scaling function coefficients. For scales high enough the samples serve as very good approximation to the first set of scaling function coefficients. This is apparent to the Haar scaling function as it is a step function. But it applies to other families of scaling function as well. There are four functions in this program, two of which to do the wavelet transform of the signal. One does the amplitude thresholding. The last reconstructs the signal using the set of lower scale scaling function coefficients and all the other sets of wavelet coefficients. The memory allocation of the arrays and display of results are done in the main program.

The procedure for removing the useless fixed pulse is shown in the flow diagram of FIG. 18.

b. Reduction of Pulse Width

The sample's surface and the interior delamination's surface are very thin boundaries. The ideal form of reflected sound signal from that surface is the f pulse. But due to the limitations of the electronic circuit bandwidth, the reflected pulse has a fixed width as shown in FIG. 19(*a*). To overcome this, one can use signal Processing to compress the signal's pulse width. The result after compression is shown in FIG. 19(*b*).

c. Elimination of Multi Reflections

The ultrasonic wave can produce multi reflections between the two reflecting surfaces which have high reflection coefficients. The adding of these multi reflection pulses to the reflected pulse will cause ghost images, as shown in FIG. 20(*a*). The first reflection in the figure is the reflection from the sample's surface. The second reflection is from the inhomogeneities within the sample. The third reflection is the second reflection from the sample's surface. This reflection overlaps with the reflection from the sample's bottom, forming ghost images. FIG. 20(*c*) shows the C scan image which has ghost images. One can follow the knowledge of acoustics, to identify the position of the reflected peak and then investigate in the reverse direction, to eliminate those reflected peak which have grater influence, and thus eliminate the multi reflections. FIG. 20(*b*) and (*d*) show the A scan and C scan images after the multi reflection elimination.

Besides the above processing method, the traditional methods of spatial filtering (such as average value filtering and mid value filtering) also are effective.

2. Projection

Projection is the nucleus of visualization technology. The visualization of the SAM data belongs to the field of 3D scalar field technology. Scalar field visualization can be divided into the categories of section surface reconstruction, equal value surface visualization and body drawing technology, after considering image formation result and efficiency and the selection of equal value surface visualization technology.

a. Equal Value Surface Visualization

An equal value surface is a series of spatial curved surfaces. The function F(x,y,z) on the curved surface has the given fixed value. Within the spatial graph, each point preserves the sampling value $F(x_I, y_I, z_k)$ at the graphic unit $(x_I, y_I, z_k)$. For each given fixed value Ft the equal value surface is the series of curved surfaces formed by all the points sFt={(x,y,z):F(x,y,z)=Ft}.

The surface reconstruction method has been used as a way to extract equal value surfaces; It uses the boundary lines of the sectional image as the basis. It is a type of sectional surface reconstruction method. The precision of the triangular plate used in this method is not so good. It is unsuitable for use in the highly fluctuating scalar field. With the increase in the capability of the PC, we have selected the more effective Marching Cube algorithm to extract equal value surface.

b. Marching Cube Algorithm

The slicing of single scan images into layers of images of the various layers of the specimen is a necessary step towards 3D volume rendering of images. The Marching Cube Algorithm uses these layers of images to stack them up to form 3D images.

Marching cube algorithm is representative of 3D data field and uses voxel unit to generate equal value surface technology. The usual algorithm to process 3D positive data field, can be represented as:

$$F_{i,j,k}=F(x_i, y_i, z_k) \ (i=1\text{-}\text{-}\text{-}, N_x, J=1, \text{-}\text{-}\text{-} N_y, k=1, \text{-}\text{-}\text{-} N=)$$

In the Marching Cube algorithm, voxel is a cubic body according to the logic. It is formed by the four pixels from each of the two neighboring layers which form a cube's eight corners. It is shown in FIG. 21.

This algorithm processes all the cubic voxel in the data field. First it carries out classification of the corners of a cube. It separates out the cube which intersects with the equal value surface. From the classification of the top points, one establishes what that cube occupies in the index within the search and classification table. A search is carried out on the distribution model of the corresponding equal value surface within the classification table. One uses interpolation to compute the intersection point of the equal value surface and the boundaries of the cube. From the corresponding positions of each of the corners of the tube and the equal value surface, one uses the intersection point of the equal value surface and the cubic body edge and follows a fixed rule to join up and form the equal value surface close to the triangular plate. One then uses interpolation to calculate the value of the normal vector of the corners of the triangular plate.

3. Drawing and Display

Open GL is a popular 3D imaging software interface suitable to use on the PC platform to produce high quality 3D images. Open GL simplifies the drawing and display procedure. It transforms the views taken, the model, the projection and visualization region and simplifies into special usage transformation coefficient, the elimination of hidden surface problem is automatically completed by the interface When withdrawing close up equal value surface triangular plates, it simultaneously calculates the vector quantity of the corners of the triangular plate. After introducing in illumination processing, then one can obtain the real effect 3D images.

Ultrascan—1 software's visualization portion and display model posseses good interaction properties. The parameters of viewing angles, sample position, light source position can be conveniently adjusted. This enables good quality 3D images.

4. The Results of the Application of Visualization Technology

Using the above visualization technology, one can display the 3D images of the structures of the samples. FIGS. 22, 23 and 24 show images produced after inspection of a flipchip, ceramic base plate and ceramic stick.

A Φ 30×15 mm aluminum sample was also inspected. The result is shown in FIG. 25(*a*). The vertical section of the sample is quite thick. So, multi-reflections and useless fixed pulse influence will be present. During the data preprocessing, the. above factors have to be eliminated and also one needs to compress the pulse width as a preprocessing step. Then one can obtain the equal value surface. The 3D image or the sample is shown in FIG. 25(*b*).

Software is written with Visual C++. The operating system is Win98.

Software functions: main dialog, file, view and test menu. Also including position process, file saving, mechanical scan and data collect, gain control signal process and image process, etc. The menu structure is shown in FIG. 26.
1. Under main menu: file, test, view and help submenu.
2. Under file submenu: new, open, print, save and exit submenu.
3. Under test submenu: system setting and start submenu. Testing parameter are set and start scanning. Under side is A scan image and upper left side is C scan image, upper right side is B scan image.
4. When a file is opened under the file menu. There are file, test, edit, view, image, window, help and display submenu. Under the edit submenu, file can be copied. Under display submenu, there are functions such as: grayscale, inverse grayscale, pseudo color, zoom in, zoom out and note. Under image submenu, there are functions such as: eliminate fixed target, reduce pulsewidth, and extract isolines, 3D image.

Advantages of this embodiment of the present invention include:
1. Increased data acquisition rate of one A/D card to such a level that it can acquire in real time the waveform of an un-modulated reflected wave. The function done by hardware is completed by software and more functions are added. C scanning SAM with single function is changed to multipurpose SAM with A, B, C image scan-and three-dimensional image functions. It is also phase SAM with software to test the phase.
2. This equipment can do analysis with multi-parameters to complete the characteristic and model identification. SAM is made as a king of quantitative testing and analysing equipment.
3. With advanced enhanced functions, hardware such as is oscilloscope, modulator and video frequency amplifier are omitted. The hardware structure is simplified a lot, reduced volume, weight and low cost and price are benefits for extending this technologies and equipment.
4. This equipment with more software is more flexible and extendable; make single functional fixed equipment developed according to the requirement of customer.

What is claimed is:

1. An acoustic lens for an acoustic microscope, including an inner metal portion, an outer glass portion and an outer metal housing, the outer glass portion having at least one opening therein, which exposes the inner metal portion, the outer metal housing serving as an outer protective housing to the outer glass portion, the glass and metal of the inner portion and outer protective housing being fused.

2. An acoustic lens according to claim 1, wherein the inner metal portion has a concave region at a position corresponding generally to the opening in the outer glass portion.

3. An acoustic lens according to claim 2, wherein a piezoelectric layer is formed over said concave region.

4. An acoustic lens according to claim 3, wherein a metallic film is formed over said piezoelectric layer, so as to form an electrode.

5. An acoustic lens according to claim 4, wherein the metallic film comprises gold.

6. An acoustic lens according to claim 5, wherein a protective layer is formed over said metallic layer.

7. An acoustic lens according to claim 6, wherein said protective layer is a high-hardness film such as silicon nitrate.

8. An acoustic lens according to claim 3, wherein said piezoelectric layer comprises one of zinc oxide, lithium niobate and silica.

9. An acoustic lens according to claim 8, wherein a metallic film is formed over said piezoelectric layer, so as to form an electrode.

10. An acoustic lens according to claim 9, wherein a protective layer is formed over said metallic layer.

11. An acoustic lens according to claim 10, wherein said protective layer is a high-hardness film such as silicon nitrate.

12. An acoustic lens according to claim 9, wherein the metallic film comprises gold.

13. An acoustic lens according to claim 12, wherein a protective layer is formed over said metallic layer.

14. An acoustic lens according to claim 13, wherein said protective layer is a high-hardness film such as silicon nitrate.

15. An acoustic lens according to claim 2, wherein said piezoelectric layer comprises one of zinc oxide, lithium niobate and silica.

16. An acoustic lens according to claim 15, wherein a metallic film is formed over said piezoelectric layer, so as to form an electrode.

17. An acoustic lens according to claim 16, wherein a protective layer is formed over said metallic layer.

18. An acoustic lens according to claim 17, wherein said protective layer is a high-hardness film such as silicon nitrate.

19. An acoustic lens according to claim 18, wherein a protective housing is provided for said outer glass portion.

20. An acoustic lens according to claim 19, wherein the glass and metal of the outer and inner portions are fused.

21. An acoustic lens according to claim 18, wherein the glass and metal of the outer and inner portions are fused.

22. An acoustic lens according to claim 1, wherein a protective housing is provided for said outer glass portion.

* * * * *